(12) United States Patent
Warby et al.

(10) Patent No.: US 8,590,750 B2
(45) Date of Patent: Nov. 26, 2013

(54) FLUID DELIVERY DEVICE

(75) Inventors: Richard Warby, Cambridgeshire (GB); Graham Hately, Norfolk (GB); Kevin Chilvers, Norfolk (GB); John Olley, Norfolk (GB); Paul Allsop, Norfolk (GB)

(73) Assignee: Consort Medical PLC, Hemel Hempstead (GB)

( * ) Notice: Subject to any disclaimer, the term of this patent is extended or adjusted under 35 U.S.C. 154(b) by 128 days.

(21) Appl. No.: 13/358,988

(22) Filed: Jan. 26, 2012

(65) Prior Publication Data

US 2012/0234861 A1 Sep. 20, 2012

(30) Foreign Application Priority Data

Mar. 16, 2011 (GB) .................................. 1104425.2

(51) Int. Cl.
*B67D 7/84* (2010.01)
(52) U.S. Cl.
USPC ........ 222/162; 222/319; 222/321.6; 222/336; 222/340; 128/200.14; 128/200.22
(58) Field of Classification Search
USPC ............. 222/162, 319, 74, 321.1, 321.6, 336, 222/340; 128/200.14, 200.22
See application file for complete search history.

(56) References Cited

U.S. PATENT DOCUMENTS

| | | | | |
|---|---|---|---|---|
| 4,079,862 A | * | 3/1978 | Fegley | ........................... 222/162 |
| 4,394,934 A | * | 7/1983 | Fegley | ............................... 222/5 |
| 5,289,818 A | * | 3/1994 | Citterio et al. | ............ 128/200.14 |
| 5,431,155 A | * | 7/1995 | Marelli | ..................... 128/200.14 |
| 6,708,846 B1 | * | 3/2004 | Fuchs et al. | ...................... 222/82 |
| 7,302,948 B2 | | 12/2007 | Anderson | |
| 7,699,052 B2 | * | 4/2010 | Schiewe et al. | .......... 128/200.22 |
| 7,731,065 B2 | | 6/2010 | Ingram et al. | |
| 8,210,167 B2 | * | 7/2012 | Corbacho | ................ 128/200.22 |
| 8,348,096 B2 | * | 1/2013 | Greiner-Perth | ................. 222/50 |
| 2001/0056259 A1 | * | 12/2001 | Skinkle et al. | ................ 604/151 |
| 2008/0210228 A1 | | 9/2008 | Corbacho | |
| 2010/0145275 A1 | | 6/2010 | Grunhut et al. | |

FOREIGN PATENT DOCUMENTS

| | | |
|---|---|---|
| EP | 1 219 356 B1 | 7/2010 |
| FR | 2682305 A1 * | 4/1993 |
| WO | 03/074189 A1 | 9/2003 |
| WO | 2004/069664 A2 | 8/2004 |

OTHER PUBLICATIONS

Combined Search and Examination Report under Sections 17 for GB 1104425.2 dated Jun. 28, 2011.

* cited by examiner

*Primary Examiner* — Kevin P Shaver
*Assistant Examiner* — Nicholas J Weiss
(74) *Attorney, Agent, or Firm* — Smith, Gambrell and Russell, LLP

(57) ABSTRACT

A fluid delivery device for discharging a fluid having a housing, a piston pump, a biasing mechanism, and a trigger mechanism. The housing has a fluid discharge outlet. The pump has a pump chamber casing for fluid storage, a piston sliding in the pump chamber, a piston plunger, and a delivery channel leading to the housing outlet. The biasing mechanism biases the piston pump casing towards the housing outlet. The trigger mechanism has a catch member and a restraining member movable by a manually actuatable trigger from a cocked to a triggered configuration. The cocked restraining member engages the catch member to prevent movement and fluid discharge. A triggered restraining member disengages from the catch member for movement of the casing towards the housing outlet to discharge fluid from housing outlet.

21 Claims, 8 Drawing Sheets

FLUID DELIVERY DEVICE

The present disclosure relates to a fluid delivery device. In particular, it relates to a fluid delivery device for nasal, sublingual or ophthalmic use.

Fluid delivery devices are well known for dispensing media such as powders and fluids for discharge into or onto the body. EP1219356 discloses one such device in which a piston pump is used for discharging a flowable media from a reservoir out of an outlet nozzle for nasal delivery. To operate the device a user manually displaces upwardly the reservoir relative to a support surface to cause a needle to form an opening in a sealing piston of the reservoir. Further manual movement of the reservoir by the user displaces the piston within the reservoir to pressurise the flowable media and cause it to be discharged via the needle.

WO2004/069664 discloses a closure member suitable for use in fluid delivery devices having a piston pump. The closure member does not require piercing by a needle. Instead one or more resilient projections on the closure member are used to seal a storage container. On actuation manual displacement of the closure member relative to the storage container causes the one or more resilient projections to deform accommodating outflow of fluid from the storage container.

In both cases the devices rely on manual displacement of at least one part of the piston pump for operation. This can lead to inconsistent discharge of media from the devices. Reasons include the different impulses and loads applied to the piston pump by different users and the possibility that a user will not fully complete the required stroke of the piston pump before releasing the device.

According to the present disclosure there is provided a fluid delivery device for discharging a fluid comprising:
  a housing;
  a piston pump;
  a biasing mechanism; and
  a trigger mechanism;
  the housing comprising an outlet for discharging the fluid;
  the piston pump comprising a casing defining a pump chamber for storage of the fluid, a piston slidably movable relative to the pump chamber, a piston plunger, and a delivery channel for delivering fluid discharged from the pump chamber to the outlet of the housing;
  the biasing mechanism acting on the casing of the piston pump to bias the casing towards the outlet of the housing;
  the trigger mechanism comprising a catch member on or connected to the casing of the piston pump and a restraining member which is movable by a manually actuatable trigger;
  the trigger mechanism being movable on operation of the manually actuatable trigger from a cocked configuration to a triggered configuration;
  wherein in the cocked configuration the restraining member is engaged with the catch member to prevent movement of the casing towards the outlet of the housing so as to prevent discharge of fluid from the pump chamber; and
  wherein in the triggered configuration the restraining member is disengaged from the catch member to enable movement of the casing towards the outlet of the housing under action of the biasing mechanism so as to discharge fluid from the pump chamber, along the delivery channel and out of the outlet of the housing.

Advantageously, the operation of the fluid delivery device is simple and consistent. The use of the trigger mechanism in combination with the biasing mechanism results in a predictable loading and impulse being applied to the casing of the piston pump. In addition, the device ensures that the piston pump undergoes a full discharge stroke under the action of the biasing mechanism. As such, partial discharges are prevented.

The restraining member may be flexible. The restraining member may be formed from a material having the ability to deform elastically.

The trigger mechanism may comprise two restraining members.

The two restraining members may extend across the housing generally perpendicularly to a longitudinal axis of the casing of the pump piston.

The two restraining members may be located on either side of the casing. In this manner, the restraining members can act to trap the casing therebetween by engagement with the catch member of the casing.

In one aspect the two restraining members may comprise a pair of arms that are outwardly bowed from each other in the cocked configuration and are capable of flexure away from each other to enable movement of the trigger mechanism into the triggered configuration. The pair of arms may be biased inwardly towards the casing in the cocked configuration to ensure reliable engagement with the catch member. This biasing effect may be produced by ensuring that the pair of arms are flexed outwardly slightly from a neutral position so as to be under some strain in the cocked configuration.

The manually actuatable trigger may comprise a thumb pad and a finger pad that, in use, can be squeezed towards one another. The thumb pad and the finger pad may be positioned on opposite sides of the housing. The thumb and finger pads may be the same size and configuration and the thumb pad may be operated by a finger and the finger pad may be operated by a thumb. Both the thumb pad and the finger pad may be movable inwardly relative to the housing. Alternatively only one pad may move inwardly relative to the housing with the other pad remaining stationary. In such a case, the stationary pad may be formed as an integral portion of the housing. The manually actuatable trigger may comprise only one pad. In such a case the one or more restraining arms of the trigger may extend from the movable pad across the interior of the device into contact with the housing or other abutment in the housing.

The thumb pad and the finger pad may be integrally formed with the restraining member.

In one aspect the finger pad and the thumb pad may be integrally formed with the two restraining members when the restraining members are in the form of a pair of arms. Advantageously, integral formation of the finger pad, thumb pad and the two restraining arms as a single moulding reduces manufacturing and assembly costs.

The catch member may comprise an outwardly extending flange of the casing. The catch member may take other forms, such as one or more projections, protrusions, teeth or similar. The catch member may be formed integrally with the casing or may be a separate component operatively connected to the casing by a suitable means, for example, welding, crimping, adhesive, etc.

The piston and the piston plunger may be fixed relative to the housing. As such, it is the casing of the piston pump that may move on actuation.

The piston and the piston plunger may be integrally formed. However, preferably, the piston plunger is formed as a separate component from the piston. On assembly, the piston and piston plunger sealingly mate with each other.

The biasing mechanism may comprise a spring acting between the housing and the casing. The spring may contact directly the housing and the casing. Alternatively, one or more intervening members may be provided to transmit the spring force to the casing.

The casing may comprise a post extending away from the outlet of the housing, the post forming a seat for receiving one end of the spring.

The piston may comprise a body and at least one resilient projection to seal the pump chamber in the cocked configuration; wherein on movement of the casing towards the outlet of the housing in the triggered configuration, the at least one resilient projection may be deflectable due to the resultant increase in pressure within the pump chamber so as to accommodate discharge of fluid from the pump chamber into the delivery channel.

The at least one resilient projection may extend around only a portion of a circumference of the piston.

At least one sealing projection axially aligned with the at least one resilient projection may extend round a remainder of the circumference of the piston.

The piston may comprise three resilient projections axially spaced apart from one another, each resilient projection extending around only a portion of a circumference of the piston, the piston further comprising three sealing projections each axially aligned with one of the three resilient projections and extending around a remainder of the circumference of the piston.

The fluid delivery device may further comprise at least one secondary sealing projection extending around the full circumference of the piston.

The fluid delivery device may comprise an upper housing defining the outlet and a lower housing which is connectable to the upper housing to define an interior of the device for containing the piston pump and the biasing mechanism.

The upper housing and lower housing may comprise a connection mechanism which enables the upper housing and lower housing to be connected together in a partially assembled configuration wherein the piston pump and the biasing mechanism span between the upper housing and the lower housing with the biasing mechanism in a first, relatively lowly compressed state; wherein the connection mechanism further enables the upper housing and lower housing to be fully assembled by moving the upper and lower housing further together to compress the biasing mechanism into a second, relatively highly compressed state.

The connection mechanism may comprise at least one detent on one of the lower or upper housing and two sets of at least one aperture in the other of the upper or lower housing, wherein the two sets of at least one aperture are axially spaced apart from one another.

The fluid delivery device may be a single-use device.

The fluid delivery device may be a nasal device, a sub-lingual device or an ophthalmic device.

There is also provided a fluid delivery device as described above combined with a single dose of fluid contained in the pump chamber. The fluid may contain a pharmaceutical.

The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl)protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, ipratropium bromide and salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for nasal inhalation and may be provided in any suitable fluid form for this purpose, for example as a solution or powder suspension in a solvent or carrier liquid, for example ethanol, or isopropyl alcohol. The pharmaceutical may alternatively be one suitable for sub-lingual or ophthalmic delivery.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. The pharmaceutical may, for example, be one which is suitable for the treatment of migraine. An example is sumatriptan. As will be appreciated, the pharmaceutical may comprise of one or more active ingredients, an example of which is flutiform. One or more surfactants may be included if desired.

The piston may be formed from an elastomer or thermoelastomer material such as EPDM, polychloroprene, hydrogenated nitrile, butyl, halo-butyl, dynamically cross-linked EPDM/PP (Santoprene®), styrenic block copolymers or blends thereof. Other suitable materials include high-density polyethylene and low-density polyethylene The housing may be formed from an engineering plastic such as polypropylene, HDPE, ABS, polyester or POM.

The casing of the piston pump may be formed from any suitable material such as glass, cyclic olefin copolymer—an example being Topas® COC available from TOPAS Advanced Polymers GmbH, Frankfurt-Höchst, Germany, or liquid crystal polymer—an example being Zenite® LCP available from DuPont, Wilmington, USA. The catch member may be formed as a moulded or machined formation on the exterior of the casing.

The restraining member and manually actuatable trigger may be formed (preferably as a single moulding) from a suitable material having the necessary flexural characteristics, such as polypropylene, HDPE, ABS, polyester or POM.

Embodiments of the present disclosure will now be described, by way of example only, with reference to the accompanying drawings in which.

Figure 1:
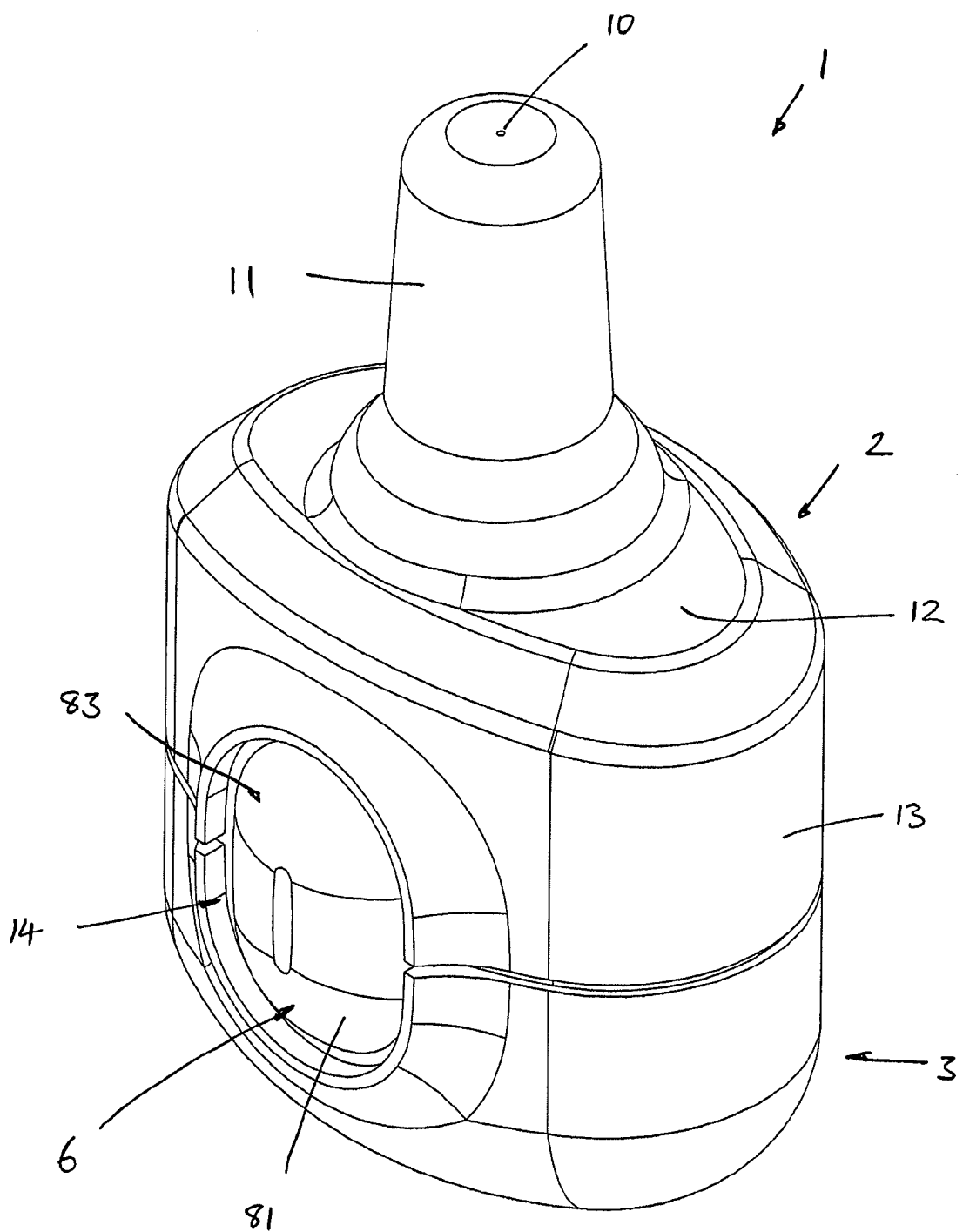
FIG. 1 is a perspective view of a first nasal device according to the present disclosure.

In the following, the fluid delivery device will be described, by way of example only, as a device suitable for nasal delivery of fluid.

As shown in the accompanying FIGS. 1 to 7, a first nasal device 1 comprises an upper housing 2, a lower housing 3, a piston pump 4, a spring 5 and a trigger mechanism 6.

Figure 2:
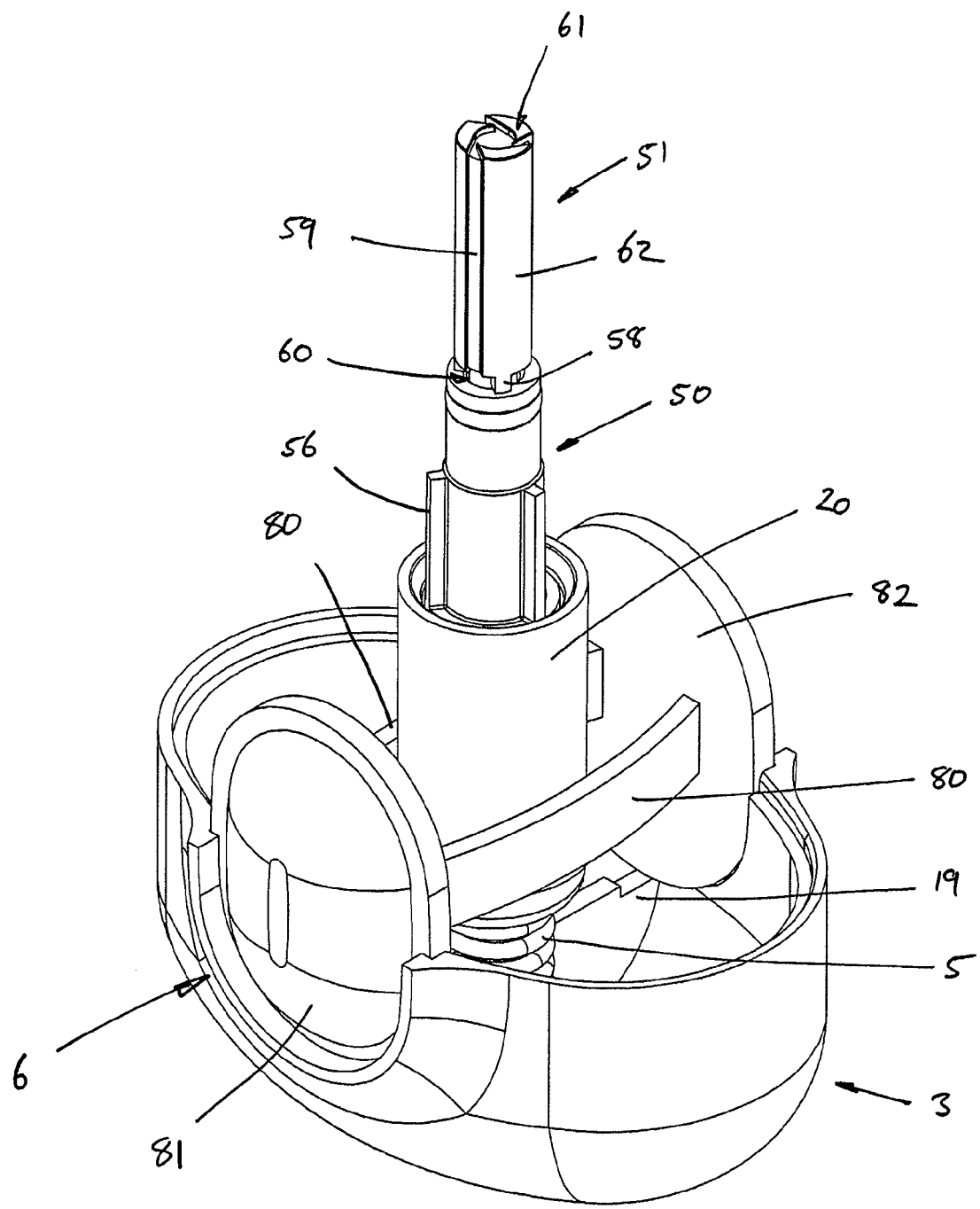
FIG. 2 is a perspective view of the nasal device of FIG. 1, with an upper housing removed.
Figure 5:
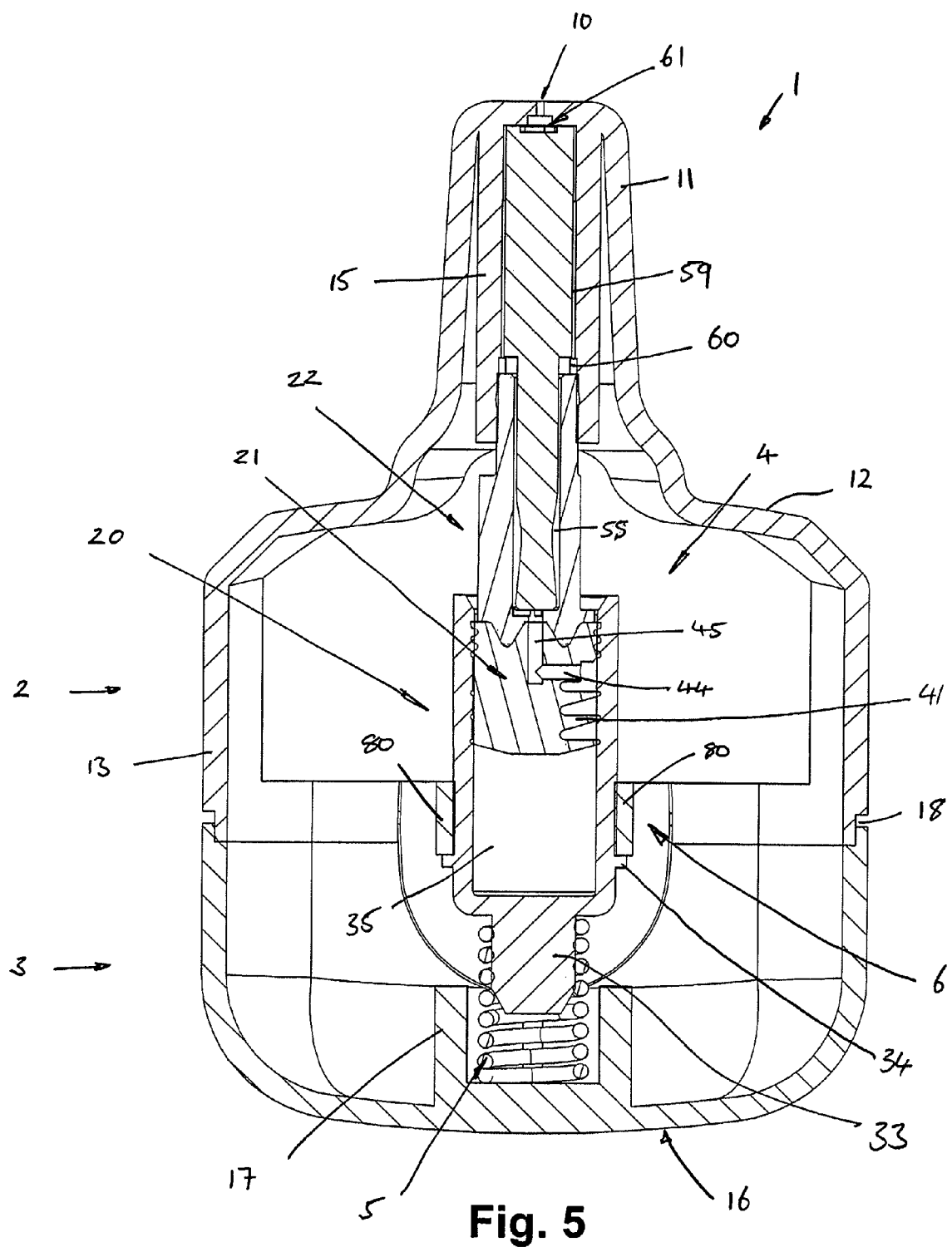
FIG. 5 is a cross-sectional view of the nasal device of FIG. 1.

The housing of the device is formed from two parts, the upper housing 2 and the lower housing 3. The upper housing 2 and lower housing 3 connect together at an interface 18 as best shown in FIG. 5 which may be a snap-fit connection or may be, for example, an ultrasonically welded connection. The housing defines an interior for containing the remaining components of the device 1. The upper housing 2 and lower housing 3 together define a side wall 13 of the housing, a base 16 and opposite the base a nasal piece 11 which extends upwardly towards an outlet orifice 10 which is provided at a distal end thereof. Shoulder portions 12 are provided between the nasal piece 11 and side wall 13. Two generally oval pad apertures 14 are provided on opposite sides of the side wall 13 of the housing, the use of which will be described further below. As best shown in the cross-sectional view of FIG. 5, the upper housing 2 is provided with an inwardly directed tubular extension 15 which extends downwardly from an upper end of the nasal piece 11 into the interior of the device 1. At the opposite end of the device, the lower housing 3 is provided with a pair of upwardly extending projections 17 which function as a spring seat as will be described further below. Further, as best shown in FIG. 2, a pair of pad support webs 19 are located at the basal end of the lower housing 3 and run from the side wall 13 generally perpendicularly towards the centre of the device 1. Use of the pad support webs 19 will be described further below.

Figure 6:
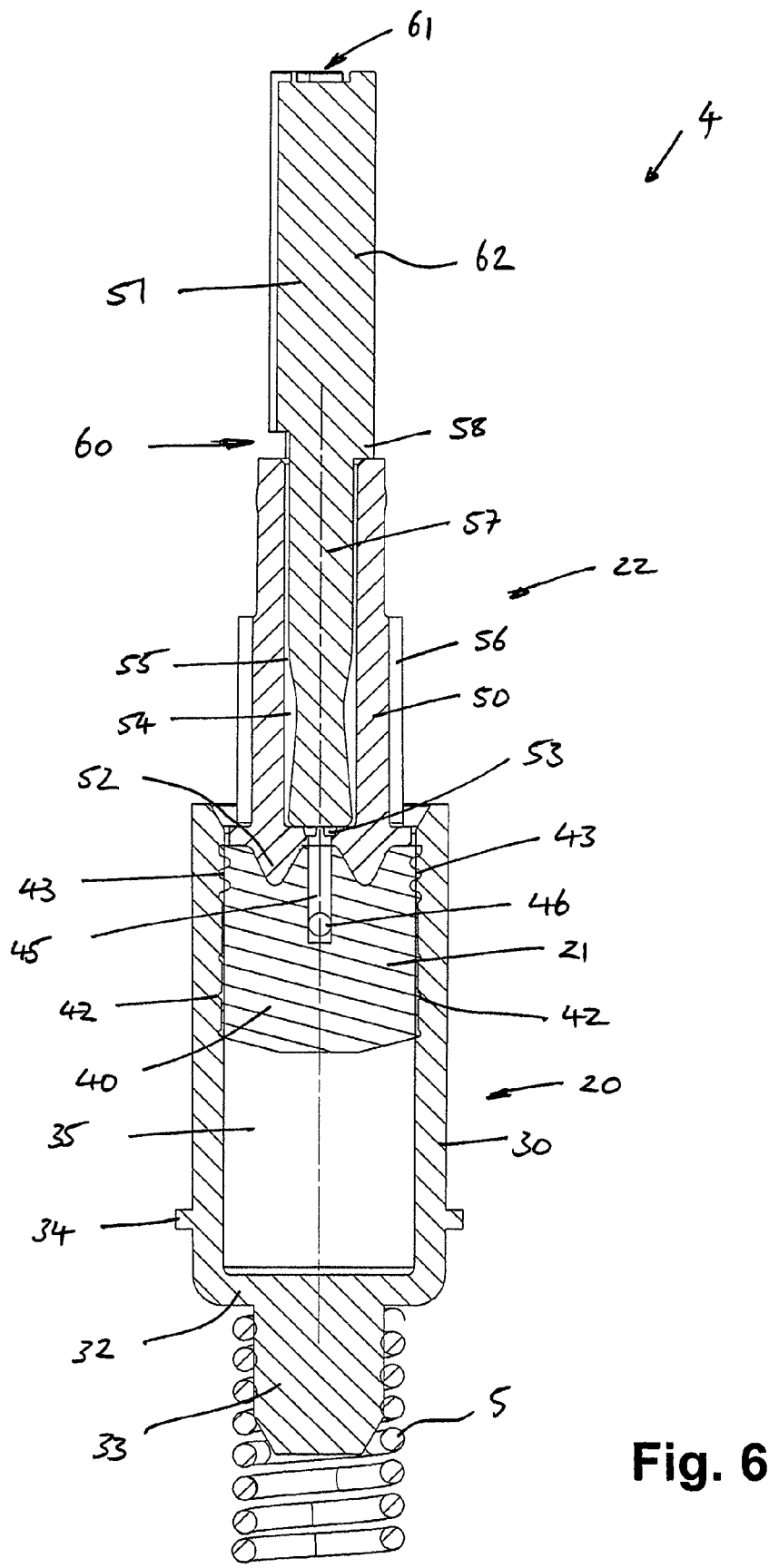
FIG. 6 is a cross-sectional view of a piston pump of the nasal device of FIG. 1.

The piston pump 4 is shown in FIG. 6 and comprises a container 20, a piston 21 and a plunger 22.

The container 20 comprises a generally cylindrical body 30 which has a closed base 32 at one end and an upper opening 31 at an end opposite the base 32. The container 20 defines a pump chamber 35 in which in use a fluid may be stored prior to discharge on operation of the device 1. Towards the base 32 of the body 30, an externally directed flange 34 is located, the use of which will be described further below. Extending axially from the base 32 is a peg extension 33 which acts as a seat for an upper end of the spring 5 as shown in FIG. 6 and on assembly in FIG. 5.

Figure 7:
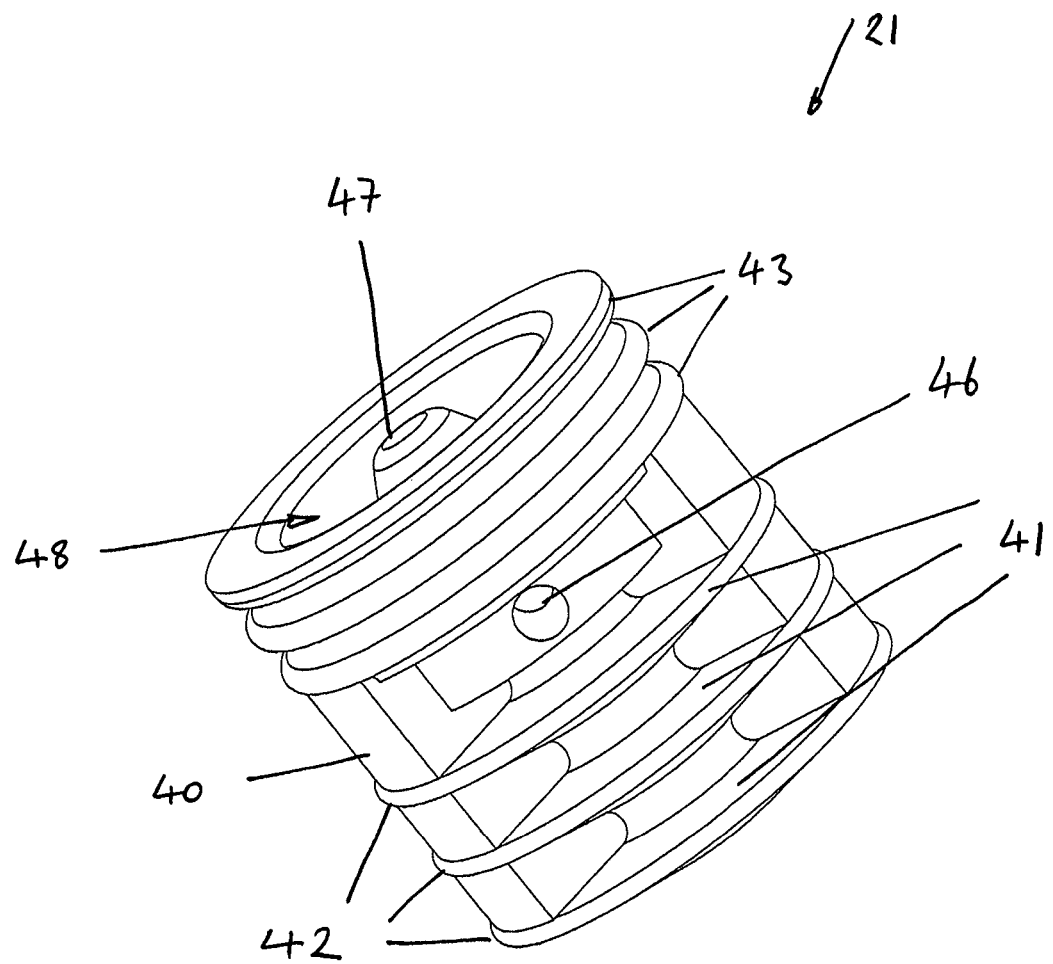
FIG. 7 is a perspective view of a piston of the nasal device of FIG. 1.

The piston 21 comprises a piston body 40 which is shown in more detail in FIG. 7. The piston body 40 is generally cylindrical but is provided with a number of shaped zones and projections for carrying out various functions. Three resilient projections 41 are provided spaced apart axially along the lower half of the piston body 40. Each resilient projection 41 extends circumferentially around a portion of the circumference of the piston body 40. In the illustrated embodiment the resilient projections 41 extend through an arc of approximately 100 degrees. The resilient projections 41 are relatively deep in the radial direction and this relatively large radial depth of the projections 41 renders them relatively flexible compared to the other sealing formations described below. The piston body 40 is further provided with three sealing projections 42 which are each axially aligned with one of the resilient projections 41 and are formed as a circumferential extension of the outward radial edge of the resilient projections 41. Each of the sealing projections 42 extend round the remainder of the circumference of the piston body 40 not coincident with the sector of the resilient projections 41. Thus in the illustrated embodiment the each sealing projection 42 extends round an arc of approximately 260 degrees. The sealing projections 42 extend radially slightly beyond the outer surface of the piston body 40. Since the 'depth' in the radial direction of the sealing projections 42 is relatively small compared to the depth of the resilient projections 41 they are relatively much less flexible.

The piston body 40 further comprises three sealing rings 43 provided at an upper end of the piston body 40 spaced axially apart from one another. In between the sealing rings 43 and the resilient projections 41 is provided an inlet port 46 which, as shown in FIG. 5, communicates with a transverse conduit 44 within the interior of the piston body 40. The transverse conduit 44 in turn communicates with an axially oriented axial conduit 45 which extends upwardly through the upper half of the piston body 40 and terminates at an outlet port 47 as shown in FIG. 7. The use of the inlet port 46 and outlet port 47 will be described further below. The upper face of the piston body 40 is provided with a circumferential recess 48 which is shaped to sealingly mate with the lower face of the plunger 22 as shown in FIG. 6.

The plunger 22 comprises a lower plunger portion 50 and an upper plunger portion 51 which are engaged with one another on assembly. If desired the engagement may be made permanent by use of a snap-fit formation or through welding or other adhesive mechanisms. The lower plunger portion 50 comprises a generally cylindrical tubular component having a centrally extending bore 54. A lower end of the bore 54 communicates with an inlet 53 which is provided at a centre of the lower end face of the plunger 22. The lower face of the lower plunger portion 50 is provided with a circumferential ridge 52 shaped to matingly engage in sealing manner with the circumferential recess 48 of the piston body 40. A plurality of axially extending strengthening ribs 56 extend up a portion of the exterior surface of the lower plunger portion 50 as shown most clearly in FIG. 2.

Figure 4:
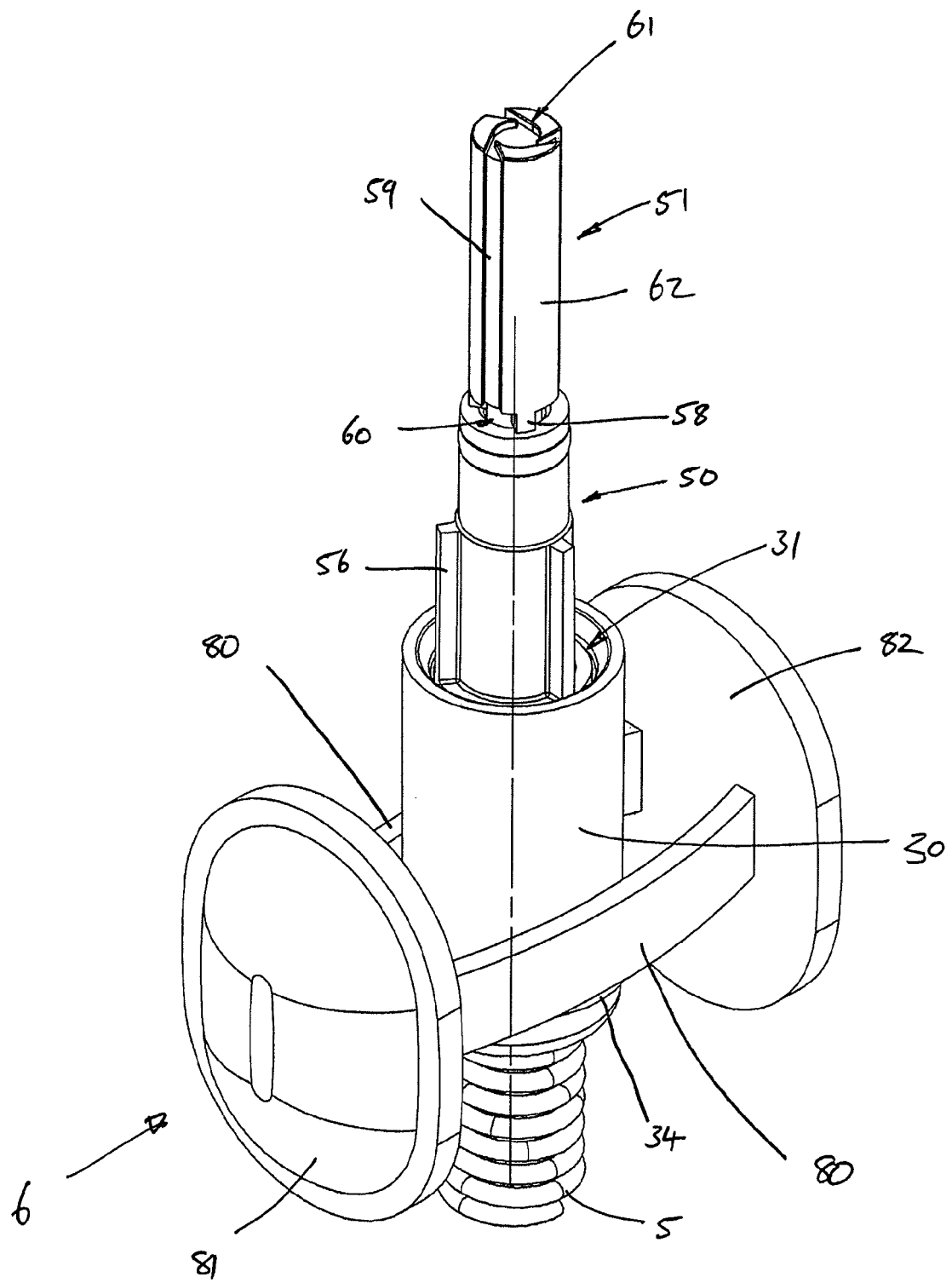
FIG. 4 is perspective view of the nasal device of FIG. 1 with the upper and lower housings removed.

The upper plunger portion 51 comprises a generally cylindrical component having a narrower plug portion 57 at a lower end and a wider upper portion 62 at an upper end. On assembly as shown in FIG. 6, the plug portion 57 is received within the bore 54 of the lower plunger portion 50 to define a lower portion 55 of a delivery channel which is annular in shape and lies between the internal surface of the lower plunger portion 50 and the exterior surface of the plug portion 57. As shown in FIGS. 2 and 4, the upper portion 62 is provided with three spacers 58 which abut against an upper edge of the lower plunge portion 50. The spacers 58 act as standoffs to create three radial ports 60 that connect the inner portion 55 of the delivery channel to an upper portion 59 of the delivery channel which is formed, as shown in FIG. 5, between an exterior face of the outer plunger portion 51 and an inner face of the tubular extension 15 of the upper housing 2. As shown in FIG. 2, this outer portion 59 of the delivery channel comprises three axially extending paths that are defined by grooves formed in the surface of the outer plunger portion 51. Each groove extends from a respective port 60 upwardly to the upper end of the plunger portion 22. As shown in FIG. 2 and FIG. 4, a swirl chamber formation 61 is provided at the upper end of the plunger 22.

As shown in FIG. 5, the piston pump 4 is located within the device 1 and extends from the distal end of the nasal piece 11 through the device 1 towards the spring seat 17. The spring 5 is positioned to extend from the base 16 of the lower housing 3 within the confines of the spring seat 17 upwardly to bear against the base 32 of the container 20 and so as to be seated securely over the peg extension 33. Thus, the spring 5 acts as a biasing mechanism to bias the container 20 upwardly towards the outlet orifice 10. It can also be noted that the engagement of the plunger 22 in the tubular extension 15 of the upper housing 2 is such that relative upward axial movement of the plunger 22 relative to the upper housing 2 is prevented. Similarly, the sealing engagement between the piston 21 and the plunger 22 means that the piston 21 is not able to move upwardly relative to the upper housing 2.

Figure 3:
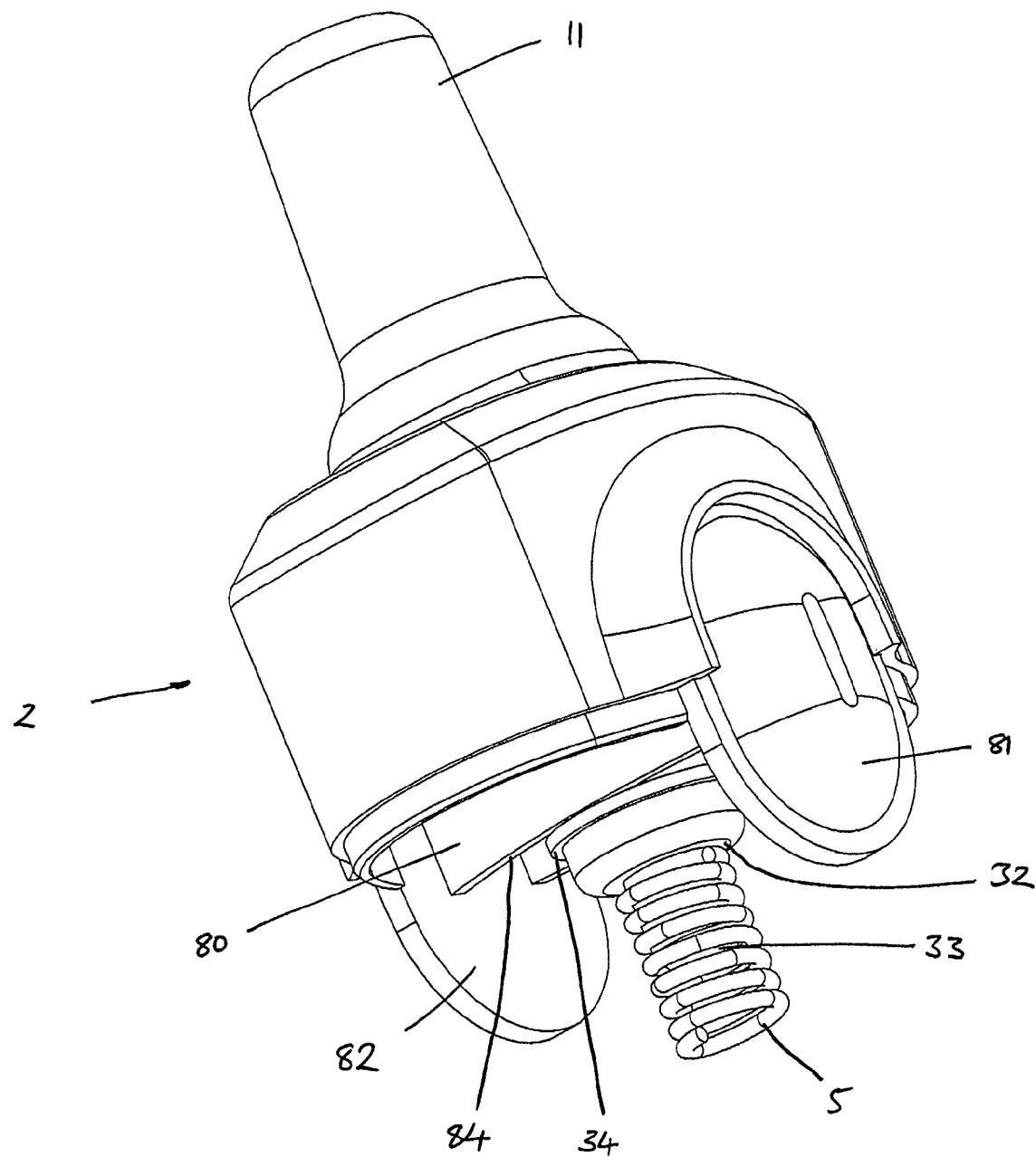
FIG. 3 is a perspective view of the nasal device of FIG. 1, with a lower housing removed.

To control actuation of the device 1 the trigger mechanism 6 is provided. As best shown in FIG. 4, the trigger mechanism 6 comprises a thumb pad 81 and a finger pad 82 which are interconnected by two restraining arms 80. Each restraining arm 80 is arcuate in shape to have a bowed configuration where each restraining arm 80 is bowed slightly away from each other. The restraining arms 80 are formed from a material having at least a degree of elastic flexibility, such as polypropylene, HDPE, ABS, polyester or POM. Preferably the thumb pad 81, finger pad 82 and restraining arms 80 are integrally formed as a single moulding. As shown in FIG. 4, on assembly the piston pump 4 passes between the restraining arms 80 and in particular such that the inner faces of the restraining arms 80 contact the exterior face of the body 30 of the container 20. In addition, lower edges 84 of the restraining arms 80 engage against the flange 34 of the container 20 as best shown in FIGS. 3 and 5. Preferably, the size and shape of the restraining arms 80 is chosen such that the restraining arms must be flexed away from each other slightly from their neutral position in order to accommodate insertion of the body 30 of the container as shown in FIG. 4. Thus, the resilient nature of the restraining arms 80 will tend to provide a small inward force on the exterior of the body 30 of the container 20 improving the grip of the restraining arms 80 on the flange 34 and preventing accidental release.

On assembly, the thumb pad 81 and finger pad 82 are positioned in the pad apertures 14 formed when the upper housing 2 and lower housing 3 are connected together as shown in FIG. 1. In addition, as shown best in FIG. 2, a lower edge of the thumb pad 81 and finger pad 82 rest on and run against an upper edge of the pad support webs 19. Similar support webs may be provided for the upper edge of the thumb pad 81 and finger pad 82 as part of the upper housing 2. The webs 19 act to guide inward movement of the pads 81 an 82 on actuation.

FIG. 5 shows the device 1 as assembled and in a 'cocked' configuration which is ready for discharge of fluid from the pump chamber 35. In the cocked configuration, the piston 21 is located in the container 20 at an upper end thereof and the resilient projections 41 together with the sealing projections 42 prevent any fluid in the pump chamber 35 reaching the inlet port 46 of the piston 21. As described above, the restraining arms 80 engage the flange 34 preventing the container 20 moving upwardly towards the outlet orifice 10.

The fluid in the pump chamber 35 comprises a single dose of fluid to be discharged. Typically, the fluid contains a pharmaceutical. The pharmaceutical may be provided as a solution or powder suspension in a solvent or carrier liquid, for example ethanol, or isopropyl alcohol.

To trigger the device 1, a user grips the thumb pad 81 and finger pad 82 between thumb and finger and squeezes the pads towards one another. This causes the restraining arms 80 to flex further apart from one another disengaging the lower edges 84 of the restraining arms 80 from the flange 34. In this triggered configuration the body 30 of the container 20 moves upwardly towards the outlet orifice 10 under the action of the spring 5. Due to the fact that the plunger 22 and piston 21 are fixed axially relative to the upper housing 2, the upward movement of the body 30 of the container 20 has the corresponding effect of trying to reduce the volume of the pump chamber 35 which results in pressurisation of the fluid within the pump chamber 35. This increase in the pressure of the fluid within the pump chamber 35 causes the resilient projections 41 to deflect upwardly allowing passage of the pressurised fluid between the resilient projections 41 and the inner face of the body 30 of the container 20. Thus, the pressurised fluid is enabled to reach the inlet port 46 of the piston body 40. The passage of fluid is only enabled through the 100 degree sector where the resilient projections 41 are located due to the relatively stiffer sealing performance of the sealing projections 42 around the remainder of the circumference of the piston body 40. In addition, pressurised fluid cannot escape fully out of the pump chamber 35 other than via inlet port 46 due to the higher sealing performance of the sealing rings 43.

Thus, pressurised fluid exits the pump chamber 35 through inlet port 46, along transverse conduit 44, along axial conduit 45 and out of outlet port 47 of the piston body 40. Due to the fact that the outlet port 47 of the piston body 40 is aligned with the inlet 53 of the plunger 22, the pressurised fluid enters the lower portion 55 of the delivery channel and is discharged upwardly between the lower plunger portion 50 and the plug portion 57 of the upper plunger portion 50. Thereafter, the pressurised fluid passes through the ports 60 into the upper portion 59 of the delivery channel between the upper portion 62 and the tubular extension 15. Finally, the pressurised fluid reaches the swirl chamber formation 61 where the fluid is forced into a rotational swirl pattern before exiting the outlet orifice 10 in the form of a spray.

As illustrated, the device 1 is a single use device which is designed to be disposed after a single discharge operation. Advantageously, the device is simple to use and can be operated even by those with low degrees of manual dexterity since a simple squeezing pincer movement between thumb and finger is all that is required. In addition, after operation, the container 20 is not accessible by the user which prevents potential misuse or abuse of the container 20 (for example, attempting to withdraw the container to access the plunger). The use of the spring 5 to provide the motive force for discharging the fluid from the pump chamber 35 provides a consistent and user-independent mechanism for discharging the fluid which provides a more consistent spray geometry out of the outlet orifice 10.

Figure 8:
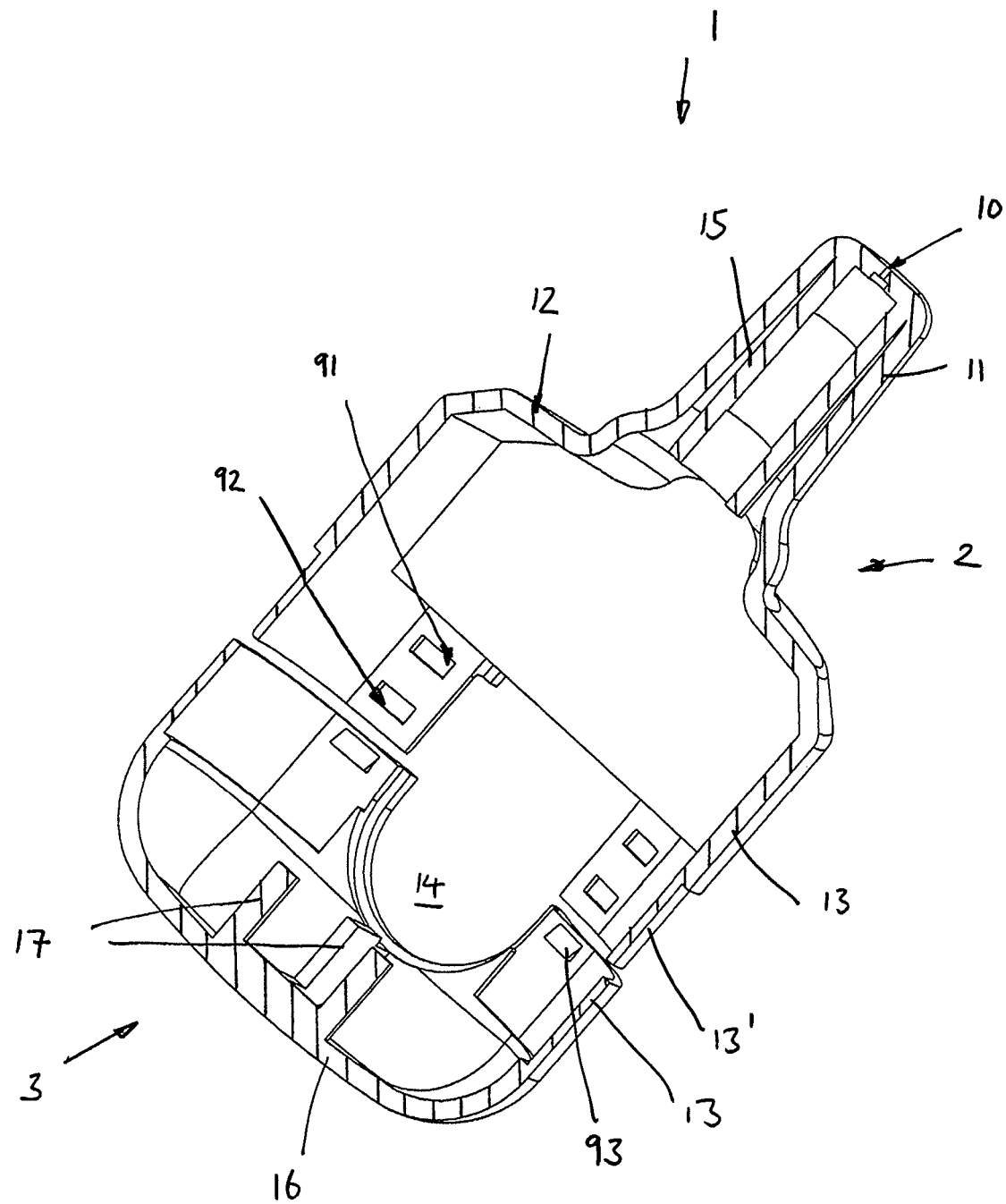
FIG. 8 is a cross-sectional view of a housing of a second nasal device according to the present disclosure.

FIG. 8 illustrates a housing of an upper housing 2 and lower housing 3 of a second nasal device 1. Like features to the first nasal device have been referenced with like reference numerals and will not be described in further detail. The reader is directed to the description above for an explanation of these features. It will also be understood that the features of the first and second nasal devices may be combined in any combination as obvious to the skilled reader and the particular combinations of features described in the first and second devices are purely illustrative.

The side wall 13 of the upper housing 2 is provided with an extended skirt portion 13' compared to the first nasal device. The skirt portion 13' is provided with a set of upper connection apertures 91 and a set of lower connection apertures 92. Each set comprises four apertures, two on each opposed side of the skirt portion 13'.

The lower housing 3 is provided with a set of four connection detents 93, two on each opposed side wall 13. Each connection detent 93 comprises an angled face on its upper side and a flat face which is generally perpendicular to the surface of the skirt portion 13' on its lower side.

On assembly the piston pump 4, spring 5 and trigger mechanism 6 are positioned within the housing 2, 3 and the lower housing 3 is engaged with the upper housing 2 such that the skirt portion 13' is received slidingly within the side wall 13 of the lower housing 3. The upper housing 2 and lower housing 3 are pushed together until the connection detents 93 engage in the lower connection apertures 92. Engagement of the detents 93 in the apertures 91 is accommodated by the inward flexing of the skirt portion 13' as the skirt portion 13' rides along and over the angled faces of the connection detents 93.

In this part-assembled configuration the upper and lower housings 2, 3 are connected together and the piston pump 4 and spring 5 span between the tubular extension 15 and the base 16 within the upwardly extending projections 17 of the spring seat. However, compared to the first nasal device, the longer distance between the base 16 and the distal end of the tubular extension 15 results in the spring 5 being relatively less compressed and thus the spring exerts a reduced force on the container 20. This can be advantageous in preventing creep of plastic components and inward creep of the piston 21 within the container 20 during storage of the device 1. Separation of the upper and lower housings 2, 3 is prevented by the flat lower face of the detents 93.

Once the device needs to be used the device can be fully assembled (by, for example, the manufacturer, an end user or pharmacist) by pushing the upper housing 2 and lower housing 3 further together which results in the connection detents 93 being pushed upwards into engagement with the upper connection apertures 91. As before this movement is accommodated by inward flexing of the skirt portion 13'. At the same time the spring 5 is fully compressed and the device is moved into the 'cocked' configuration.

It should be noted that the presence of the restraining arms 80 of the trigger mechanism 6 prevent upward movement of the container 20 during the assembly steps.

Actuation of the second nasal device is the same as that described above.

The invention claimed is:

1. A fluid delivery device for discharging a fluid comprising:
   a housing;
   a piston pump;
   a biasing mechanism; and
   a trigger mechanism;
   the housing comprising an outlet for discharging the fluid;
   the piston pump comprising a casing defining a pump chamber for storage of the fluid, a piston slidably movable relative to the pump chamber, a piston plunger, and a delivery channel for delivering fluid discharged from the pump chamber to the outlet of the housing;
   the biasing mechanism acting on the casing of the piston pump to bias the casing towards the outlet of the housing;
   the trigger mechanism comprising a catch member on or connected to the casing of the piston pump and a restraining member which is movable by a manually actuatable trigger;
   the trigger mechanism being movable on operation of the manually actuatable trigger from a cocked configuration to a triggered configuration;
   wherein in the cocked configuration the restraining member is engaged with the catch member to prevent movement of the casing towards the outlet of the housing so as to prevent discharge of fluid from the pump chamber; and
   wherein in the triggered configuration the restraining member is disengaged from the catch member to enable movement of the casing towards the outlet of the housing under action of the biasing mechanism so as to discharge fluid from the pump chamber, along the delivery channel and out of the outlet of the housing.

2. The fluid delivery device of claim 1 wherein the restraining member is flexible.

3. The fluid delivery device of claim 1 wherein the trigger mechanism comprises two restraining members.

4. The fluid delivery device of claim 3 wherein the two restraining members extend across the housing generally perpendicularly to a longitudinal axis of the casing of the pump piston.

5. The fluid delivery device of claim 3 wherein the two restraining members are located on either side of the casing.

6. The fluid delivery device of claim 3 wherein the two restraining members comprise a pair of arms that are outwardly bowed from each other in the cocked configuration and are capable of flexure away from each other to enable movement of the trigger mechanism into the triggered configuration.

7. The fluid delivery device of claim 1 wherein the manually actuatable trigger comprises a thumb pad and a finger pad that, in use, can be squeezed towards one another.

8. The fluid delivery device of claim 7 wherein the thumb pad and the finger pad are integrally formed with the restraining member.

9. The fluid delivery device of claim 6 as wherein the manually actuatable trigger comprises a thumb pad and a finger pad, wherein the finger pad and the thumb pad are integrally formed with the pair of arms.

10. The fluid delivery device of claim 1 wherein the catch member comprises an outwardly extending flange of the casing.

11. The fluid delivery device of claim 1 wherein the piston and the piston plunger are fixed relative to the housing.

12. The fluid delivery device of claim 1 wherein the biasing mechanism comprises a spring acting between the housing and the casing.

13. The fluid delivery device of claim 12 wherein the casing comprises a post extending away from the outlet of the housing, the post forming a seat for receiving one end of the spring.

14. The fluid delivery device of claim 1 wherein the piston comprises a body and at least one resilient projection to seal the pump chamber in the cocked configuration; wherein on movement of the casing towards the outlet of the housing in the triggered configuration, the at least one resilient projection is deflectable due to the resultant increase in pressure within the pump chamber so as to accommodate discharge of fluid from the pump chamber into the delivery channel.

15. The fluid delivery device of claim 14 wherein the at least one resilient projection extends around only a portion of a circumference of the piston.

16. The fluid delivery device of claim 15 wherein at least one sealing projection axially aligned with the at least one resilient projection extends round a remainder of the circumference of the piston.

17. The fluid delivery device of claim 1 wherein the housing comprises an upper housing defining the outlet and a lower housing which is connectable to the upper housing to define an interior of the device for containing the piston pump and the biasing mechanism.

18. The fluid delivery device of claim 17 wherein the upper housing and lower housing comprise a connection mechanism which enables the upper housing and lower housing to be connected together in a partially assembled configuration wherein the piston pump and the biasing mechanism span between the upper housing and the lower housing with the biasing mechanism in a first, relatively lowly compressed state; wherein the connection mechanism further enables the upper housing and lower housing to be fully assembled by moving the upper and lower housing further together to compress the biasing mechanism into a second, relatively highly compressed state.

19. The fluid delivery device of claim 18 wherein the connection mechanism comprises at least one detent on one of the lower or upper housing and two sets of at least one aperture in the other of the upper or lower housing, wherein the two sets of at least one aperture are axially spaced apart from one another.

20. The fluid delivery device of claim 1 wherein the device is a single-use device.

21. The fluid delivery device of claim 1 combined with a single dose of fluid contained in the pump chamber.

* * * * *